(12) United States Patent
Nagahara et al.

(10) Patent No.: US 12,702,318 B2
(45) Date of Patent: Aug. 11, 2026

(54) ENDOSCOPE SYSTEM FOR MEASURING BLOOD FLOW VELOCITY IN GASTROINTESTINAL SUPERFICIAL SMALL BLOOD VESSEL

(71) Applicant: JUNTENDO EDUCATIONAL FOUNDATION, Tokyo (JP)

(72) Inventors: Akihito Nagahara, Bunkyo-ku (JP); Hiroya Ueyama, Bunkyo-ku (JP); Yoichi Akazawa, Bunkyo-ku (JP)

(73) Assignee: JUNTENDO EDUCATIONAL FOUNDATION, Tokyo (JP)

( * ) Notice: Subject to any disclaimer, the term of this patent is extended or adjusted under 35 U.S.C. 154(b) by 101 days.

(21) Appl. No.: 18/708,089

(22) PCT Filed: Nov. 8, 2022

(86) PCT No.: PCT/JP2022/041538
§ 371 (c)(1),
(2) Date: May 7, 2024

(87) PCT Pub. No.: WO2023/085262
PCT Pub. Date: May 19, 2023

(65) Prior Publication Data
US 2025/0169707 A1 May 29, 2025

(30) Foreign Application Priority Data
Nov. 9, 2021 (JP) ................................ 2021-182768

(51) Int. Cl.
*A61B 5/026* (2006.01)
*A61B 1/273* (2006.01)
(Continued)

(52) U.S. Cl.
CPC .......... *A61B 5/0261* (2013.01); *A61B 1/2736* (2013.01); *G06T 7/0012* (2013.01);
(Continued)

(58) Field of Classification Search
CPC ........ A61B 1/3137; G06T 2207/10016; G06T 2207/10068; G06T 2207/30028;
(Continued)

(56) References Cited

U.S. PATENT DOCUMENTS 10,304,188 B1 * 5/2019 Kumar ................. G06V 20/695
2013/0211195 A1 * 8/2013 Yao ...................... A61K 31/685
600/101

(Continued)

FOREIGN PATENT DOCUMENTS

JP 4-17076 A 1/1992
JP 2014-4329 A 1/2014

(Continued)

OTHER PUBLICATIONS

International Search Report issued Jan. 24, 2023, in PCT/JP2022/041538, 2 pages.

(Continued)

*Primary Examiner* — Gerald Johnson
(74) *Attorney, Agent, or Firm* — Oblon, McClelland, Maier & Neustadt, L.L.P.

(57) ABSTRACT

To provide means for measuring the blood flow rate of gastric subepithelial microvessel in real time. An endoscope system for measuring the blood flow rate of gastric subepithelial microvessel comprises a magnifying endoscope and a blood flow video data processing unit for processing blood flow video data obtained using the magnifying endoscope, and (A) the magnifying endoscope shoots a blood flow video of the gastric subepithelial microvessel and transmits the blood flow video to the blood flow video data processing unit, and (B) after receiving the blood flow video, the blood flow video data processing unit performs the following data processing (B1) to (B5): (B1) processing of decomposing the obtained blood flow video into frames, (B2) processing
(Continued)

of removing a translation component by comparing an image of frame 1 and an image of subsequent frame 2, (B3) processing of calculating a difference in a red component between the images from which the translation component has been removed, (B4) processing of segmenting a part for which the difference in the red component has been calculated, and (B5) processing of calculating a segment size of obtained segment data.

17 Claims, 3 Drawing Sheets

(51) Int. Cl.
*G06T 7/00* (2017.01)
*G06T 7/11* (2017.01)
*G06T 7/246* (2017.01)
*G06T 7/90* (2017.01)

(52) U.S. Cl.
CPC ................ *G06T 7/11* (2017.01); *G06T 7/248* (2017.01); *G06T 7/90* (2017.01); *G06T 2207/10016* (2013.01); *G06T 2207/10068* (2013.01); *G06T 2207/30104* (2013.01)

(58) Field of Classification Search
CPC . G06T 2207/30096; G06T 2207/30104; G06T 7/0012; G06T 7/11
See application file for complete search history.

(56) References Cited

U.S. PATENT DOCUMENTS

2013/0323673 A1 12/2013 Hakomori et al.
2017/0258296 A1 9/2017 Kaku
2018/0206738 A1 7/2018 Kamon
2019/0073769 A1* 3/2019 Watanabe .......... A61B 1/00045
2019/0274518 A1 9/2019 Themelis et al.
2022/0378394 A1* 12/2022 Yamamoto ............. A61B 8/488

FOREIGN PATENT DOCUMENTS

JP 2019-520879 A 7/2019
WO WO 2016/121811 A1 8/2016
WO WO 2017/061256 A1 4/2017

OTHER PUBLICATIONS

Hiroya Ueyama, et al., S01-2-5 consideration of Blood Flow Velocity in the Stomach Superficial microvessel with a Magnifying Endoscope, 97th Congress of Japan Gastroenterological Endoscopy Society (JGES 2019), vol. 61, 4 pages (with English Translation).
Baha Moshiree, MD, et al., "Gastroparesis Dietary Recommendations in Patients with Gastroparesis-Like Symptoms are Only Effective in Normal Colon Transit Documented by Wireless Motility Capsule Methodology", American College of Gastroenterology, Oct. 25, 2019-Oct. 30, 2019, pp. S681-S682.
Noboru Yatagai et al., Gastroenterology W16-7, Examination of Blood Flow Velocity in the Stomach Superficial Microvessel by Magnifying Endoscope Observation (Young Scientist Award), 28th Japan Digestive Disease Week (JDDW 2020), 4 pages (with English Translation).
Hiroya Ueyama et al., "Dynamic diagnosis of early gastric cancer with microvascular blood flow rate using magnifying endoscopy (with video): A pilot study", J Gastroenterol Hepatol. 2021; 36(7): 1927-1934, doi: 10.1111/jgh. 15425, pp. 1-8.

* cited by examiner

< RESULT SAMPLES >

INPUT FRAME 1

INPUT FRAME 2

(*BLACK CIRCLES IN IMAGES WERE ADDED AFTERWARDS TO EMPHASIZE SITE OF DIFFERENCE)

DIFFERENCE IN RED COMPONENT (*WHITE CIRCLE IN IMAGE WAS ADDED AFTERWARDS TO INDICATE SITE OF BLACK CIRCLE IN INPUT FRAME)

ENDOSCOPE SYSTEM FOR MEASURING BLOOD FLOW VELOCITY IN GASTROINTESTINAL SUPERFICIAL SMALL BLOOD VESSEL

CROSS-REFERENCE TO RELATED APPLICATIONS

This application is a National Phase entry of Japanese PCT Application PCT/JP2022/041538, filed on Nov. 8, 2022, which claims priority to Japanese Patent Application No. JP2021-182768, filed on Nov. 9, 2021. The entire contents of each of these applications are incorporated herein by reference.

TECHNICAL FIELD

The present invention relates to an endoscope system for measuring the blood flow rate of gastric subepithelial microvessel.

BACKGROUND ART

With recent advances in endoscope devices and technologies, the magnifying endoscopic diagnostic scheme has been established, and qualitative diagnosis of gastrointestinal lesions is carried out based on the microvascular architecture and microsurface structure of the gastric subepithelial. However, it is a static diagnostic scheme based on still images. Although the blood flow (movement of red blood cells) in subepithelial microvessels has been observed using the magnifying endoscope, how gastrointestinal lesions change the blood flow compared with the blood flow in the normal mucosa has not been considered. Dynamic endoscopic diagnosis of biological functions of the gastrointestinal mucosa will be a new evaluation method for diagnosis and pathological elucidation of various gastrointestinal lesions including gastrointestinal carcinoma, and can enable diagnosis of lesions which are difficult to be diagnosed in the conventional static diagnostic scheme or lesions which are technically difficult to be diagnosed.

The present inventors have measured the blood flow rate of subepithelial microvessels in the stomach using a magnifying endoscope and found and reported that the blood flow rate of subepithelial microvessels in the stomach is useful for qualitative magnifying endoscopic diagnosis of early gastric cancer (Non Patent Literatures 1 to 4).

CITATION LIST

Non Patent Literature

Non Patent Literature 1
97th Congress of Japan Gastroenterological Endoscopy Society (JGES 2019)
Non Patent Literature 2
American College of Gastroenterology, Oct. 25, 2019-Oct. 30, 2019
Non Patent Literature 3
28th Japan Digestive Disease Week (JDDW 2020)
Non Patent Literature 4
J Gastroenterol Hepatol. 2021; 36 (7): 1927-1934, doi: 10.1111/jgh. 15425.

SUMMARY OF INVENTION

Technical Problem

However, the method of measuring the microvascular blood flow rate involves post analysis and is inefficient, and there is a demand for new means of measuring the blood flow rate of gastric subepithelial microvessel in real time for clinical practice.

Thus, an object of the present invention is to provide an endoscope system for measuring the blood flow rate of gastric subepithelial microvessel in real time.

Solution to Problem

In a study to measure the blood flow rate of gastric subepithelial microvessel in real time, the present inventors have found that the blood flow rate of gastric subepithelial microvessel can be measured in real time when a software-based method is used to measure the blood flow rate in a magnifying endoscopic video and a movement of a red component, which indicates a movement of a red blood cell, is measured in a blood flow video during image processing. And the present inventors made the present invention based on this finding.

Specifically, the present invention provides the following inventions [1] to [16].

[1] An endoscope system for measuring a blood flow rate of gastric subepithelial microvessel, the endoscope system comprising a magnifying endoscope and a blood flow video data processing unit for processing blood flow video data obtained with the magnifying endoscope, wherein (A) the magnifying endoscope shoots a blood flow video of gastric subepithelial microvessel and transmits the blood flow video to the blood flow video data processing unit, and (B) after receiving the blood flow video, the blood flow video data processing unit performs the following data processing (B1) to (B5):

(B1) processing of decomposing the obtained blood flow video into frames;

(B2) processing of removing a translation component by comparing an image of frame 1 and an image of subsequent frame 2;

(B3) processing of calculating a difference in a red component between the images from which the translation component has been removed;

(B4) processing of segmenting a part for which the difference in the red component has been calculated; and (B5) processing of calculating a segment size of obtained segment data.

[2] The endoscope system according to [1], wherein the blood flow video data is blood flow video data of microvessel in a part of a gastric subepithelial suspected to have an abnormality obtained using the magnifying endoscope.

[3] The endoscope system according to [2], wherein the endoscope system further performs processing of comparing an obtained blood flow rate of gastric subepithelial microvessel and a blood flow rate of normal gastric subepithelial microvessel.

[4] The endoscope system according to any one of [1] to [3], wherein the processing of removing a translation component is processing of detecting a difference between frames caused by a blood flow.

[5] The endoscope system according to any one of [1] to [4], wherein the processing of calculating the difference in the red component is to detect a movement of a red blood cell.

[6] The endoscope system according to any one of [1] to [5], wherein a segment generated by the segmentation is a segment through which a red blood cell passes between the frame 1 and the frame 2.

[7] The endoscope system according to any one of [1] to [6], wherein the calculation of the segment size is a calculation of a minor axis and a major axis of the segment.

[8] The endoscope system according to any one of [1] to [7], wherein a flow rate in each segment in the frame 2 is calculated based on the segment size and a time between the frame 1 and the frame 2.

[9] A method of measuring a blood flow rate of gastric subepithelial microvessel, comprising: a step of shooting a blood flow video of gastric subepithelial microvessel using a magnifying endoscope;

a step of decomposing the obtained blood flow video into frames;

a step of removing a translation component by comparing an image of frame 1 and an image of subsequent frame 2;

a step of calculating a difference in a red component between the images from which the translation component has been removed;

a step of segmenting a part for which the difference in the red component has been calculated; and a step of calculating a segment size of obtained segment data.

[10] The measuring method according to [9], wherein the blood flow video is a blood flow video of microvessel in a part of a gastric subepithelial suspected to have an abnormality obtained using the magnifying endoscope.

[11] The measuring method according to [10], further comprising:

a step of comparing an obtained blood flow rate of gastric subepithelial microvessel and a blood flow rate of normal gastric subepithelial microvessel.

[12] The measuring method according to any one of [9] to [11], wherein the step of removing the translation component is a step of detecting a difference between frames caused by a blood flow.

[13] The measuring method according to any one of [9] to [12], wherein the step of calculating the difference in the red component is to detect a movement of a red blood cell.

[14] The measuring method according to any one of [9] to [13], wherein a segment generated by the segmentation is a segment through which a red blood cell passes between the frame 1 and the frame 2.

[15] The measuring method according to any one of [9] to [14], wherein the calculation of the segment size is performed by calculating a minor axis and a major axis of the segment.

[16] The measuring method according to any one of [9] to [15], wherein a flow rate in each segment in the frame 2 is calculated based on the segment size and a time between the frame 1 and the frame 2.

Advantageous Effects of Invention

With the endoscope system and method according to the present invention, the blood flow rate of gastric subepithelial microvessel can be measured in real time using a magnifying endoscope, so that it is possible to diagnose and pathologically elucidate, in early stages, neoplastic lesions and non-neoplastic lesions of gastrointestinal tracts, inflammatory bowel diseases, inflammatory diseases and functional diseases of gastrointestinal tracts, allergic gastrointestinal diseases, and abnormal gastrointestinal perfusion caused by lifestyle diseases other than gastrointestinal diseases.

DESCRIPTION OF EMBODIMENTS

Figure 1:
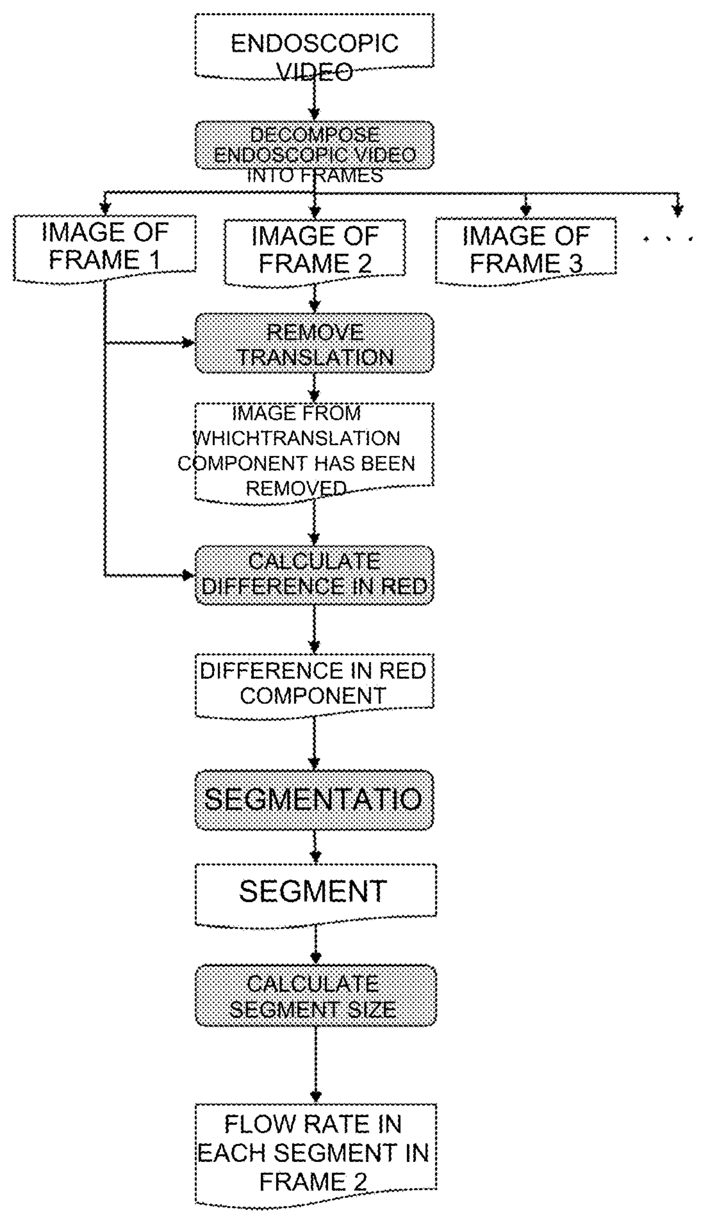
FIG. 1 is a flow diagram of a process in which the endoscope system according to the present invention determines the blood flow rate in frame 2 based on frame 2 and frame 1 of an endoscopic video. In this drawing, gray boxes indicate processing means, and white boxes indicate data.
Figure 1:
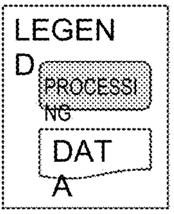

An aspect of the present invention is an endoscope system for measuring the blood flow rate of gastric subepithelial microvessel, the endoscope system comprising a magnifying endoscope and a blood flow video data processing unit for processing blood flow video data obtained using the magnifying endoscope, wherein (A) the magnifying endoscope shoots a blood flow video of gastric subepithelial microvessel and transmits the blood flow video to the blood flow video data processing unit, and (B) after receiving the blood flow video, the blood flow video data processing unit performs the following data processing (B1) to (B5):

(B1) processing of decomposing the obtained blood flow video into frames, (B2) processing of removing a translation component by comparing an image of frame 1 and an image of subsequent frame 2, (B3) processing of calculating a difference in a red component between the images from which the translation component has been removed, (B4) processing of segmenting a part for which the difference in the red component has been calculated, and (B5) processing of calculating a segment size of obtained segment data.

Another aspect of the present invention is a method of measuring the blood flow rate of gastric subepithelial microvessel in real time while shooting a video of gastric subepithelial microvessel, the method comprising the following steps (a) to (f):

(a) a step of shooting a blood flow video of gastric subepithelial microvessel with a magnifying endoscope, (b) a step of decomposing the obtained blood flow video into frames, (c) a step of removing a translation component by comparing an image of frame 1 and an image of subsequent frame 2, (d) a step of calculating a difference in a red component between the images from which the translation component has been removed, (e) a step of segmenting a part for which the difference in the red component has been calculated, and (f) a step of calculating a segment size of obtained segment data.

By further performing processing or a step of comparing the obtained blood flow rate of gastric subepithelial microvessel v and the blood flow rate of normal gastric subepithelial microvessel, whether a carcinoma or the like has occurred in the gastrointestinal tract can be diagnosed.

The processing (A) that the magnifying endoscope shoots a blood flow video of gastric subepithelial microvessel and transmits the blood flow video to the blood flow video data processing unit in the system according to the present invention and the step (a) of shooting a blood flow video of gastric subepithelial microvessel using a magnifying endoscope in the method according to the present invention are both performed using a magnifying endoscope.

Any magnifying endoscope can be used as long as it can measure a blood flow in a microvessel. Commercially available magnifying endoscopes usually have a video shooting function.

The data processing (B1) to (B5) in the system according to the present invention and the steps (b) to (f) in the method according to the present invention are substantially the same, so that the steps in the method according to the present invention will be described.

FIG. 1 shows a specific example of a process flow.

The step (a) in the present invention, is a step of shooting a blood flow video of a microvessel in a part of a gastric subepithelial suspected to have an abnormality using a magnifying endoscope. Any magnifying endoscope can be used as long as it can measure a blood flow in a microvessel. Commercially available magnifying endoscopes usually have a video shooting function.

The steps (b) to (f) in the present invention can be performed in real time by a computer which has received the blood flow video obtained using the magnifying endoscope.

Any known software can be used as a framework used for image processing in the present invention. For example, OpenCV or dlib can be used. Development languages, such as c/c++, Python or JavaScript, can be used.

Image processing software is preferably run by specifying the following three arguments.

TABLE 1

| Order of arguments | Content | Description |
|---|---|---|
| 1 | Video to be analyzed | Video file taken using an endoscope to be used for flow rate measurement is specified. |
| 2 | Red component difference threshold | In calculation of difference in red component between frames, pixels are determined to have a difference when difference in red component between the pixels is equal to or more than this threshold. |
| 3 | Minimum segment threshold | Of segments finally obtained, segment smaller than this threshold is removed as noise. |

The step (b) is a step of decomposing the blood flow video obtained using the magnifying endoscope into frames.

In this step, a video file taken using the magnifying endoscope, which is to be analyzed, is specified, and the video is decomposed into frames. In this step, as shown in FIG. 1, images of the video are separated into an image of frame 1, an image of frame 2, an image of frame 3 and the like.

The step (c) is (c) a step of removing a translation component by comparing an image of frame 1 and an image of subsequent frame 2.

In this operation, such an image is obtained that a translation component between the image of frame 1 and the image of frame 2 was removed (see FIG. 1). In this step, a part in which there is a difference between the image of frame 1 and the image of frame 2, that is, a difference between the frames which is caused by the blood flow, is detected (see FIG. 2).

The step (d) is a step of calculating a difference in a red component between the images from which the translation component has been removed.

In this step, a difference between the image of frame 1 and the image of frame 2, that is, a difference between the frames which is caused by the blood flow, is calculated in terms of the red component. A movement of a red component means a movement of a red blood cell in the blood, and therefore, a movement of a red blood cell can be detected by calculating the difference in the red component.

When calculating the difference in the red component between the frames in this step, pixels are determined to have a difference when the difference in the red component between the pixels is equal to or more than a certain level. Therefore, a red component threshold is preferably set in advance.

The step (e) is a step of segmenting a part for which the difference in the red component has been calculated.

In this step, a segment through which a red blood cell passes between the frame 1 and the frame 2 is determined.

The step (f) is calculating a segment size of obtained segment data.

In this step, a minor axis and a major axis are measured as the segment size.

Through the steps described above, the blood flow rate can be measured in each segment in the frame 2. In addition, as shown in Table 2, the blood flow rate can also be measured in each segment in other frames of the obtained video. Whether the gastric subepithelial has a disease, such as an early-stage carcinoma, can be diagnosed by comparing the blood flow rate thereof with the blood flow rate of normal gastric subepithelial microvessel. The comparison of the blood flow rates can also be performed by the computer which performs the steps (b) to (f) described above.

Examples of the gastrointestinal tract include esophagus, stomach, duodenum, small intestine, colon and a rectum. Examples of the gastrointestinal disease include neoplastic lesions such as esophageal cancer, gastric cancer, duodenal cancer, colorectal cancer and rectal cancer, non-neoplastic lesions such as stomach polyp and colon polyp, inflammatory bowel diseases such as ulcerative colitis and Crohn's disease, inflammatory diseases and functional diseases such as esophagitis, gastritis, functional dyspepsia, irritable bowel syndrome, chronic constipation, diarrhea and abnormal bowel movement, allergic gastrointestinal diseases, and abnormal gastrointestinal perfusion caused by lifestyle diseases other than gastrointestinal diseases.

Figure 4:
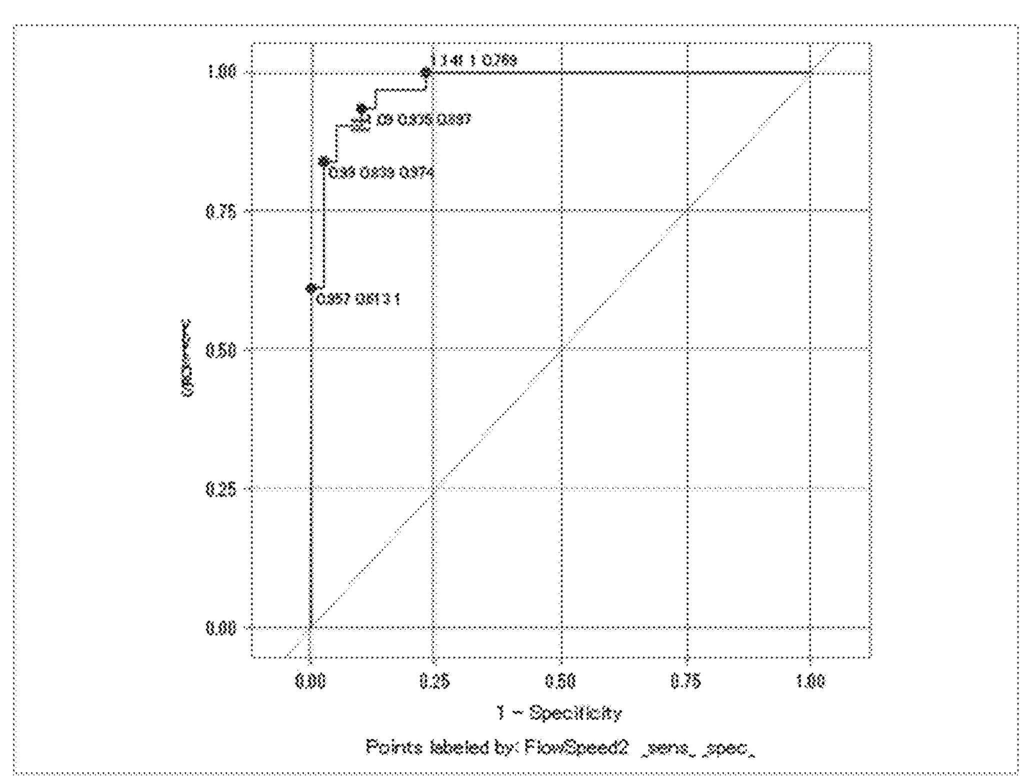
FIG. 4 shows a ROC analysis result for an average blood flow rate in the case of early gastric cancer and an average blood flow rate of normal gastric subepithelial microvessel.

In the case of early gastric cancer, for example, the blood flow rate was statistically significantly lower and falls within a narrower range than the blood flow rate of normal gastric subepithelial microvessel, even though individual variations were taken into account. Furthermore, an ROC analysis of averages of the blood flow rate shows that the cut-off value was 1.09 as shown in FIG. 4 (the sensitivity was 90.3% and the specificity was 89.7%).

EXAMPLE

Next, the present invention will be described in more detail with reference to an example. However, the present invention is not limited to this example.

Example 1

A magnifying endoscopic video of a gastric mucosa was processed according to the flow shown in FIG. 1 by using Python as the development language, using OpenCV as the framework for image processing and specifying the three arguments in Table 1 described above. The magnifying endoscopic video was shot using an endoscope system LASEREO 7000 series (FUJIFILM Corporation) and a scope EG-L600ZW7 (FUJIFILM Corporation).

Figure 2:
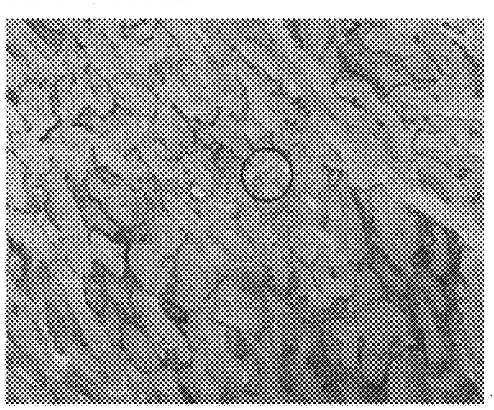
FIG. 2 shows frame 1 and frame 2 from which translation component was removed.
Figure 2:
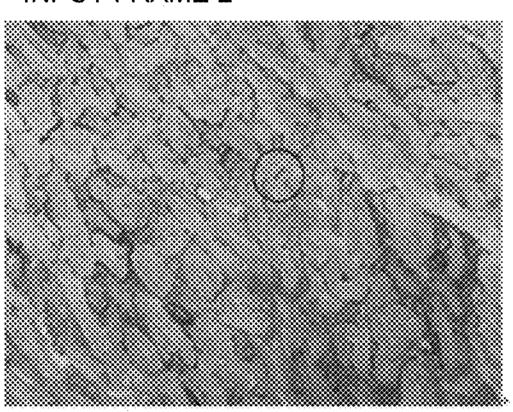
Figure 3:
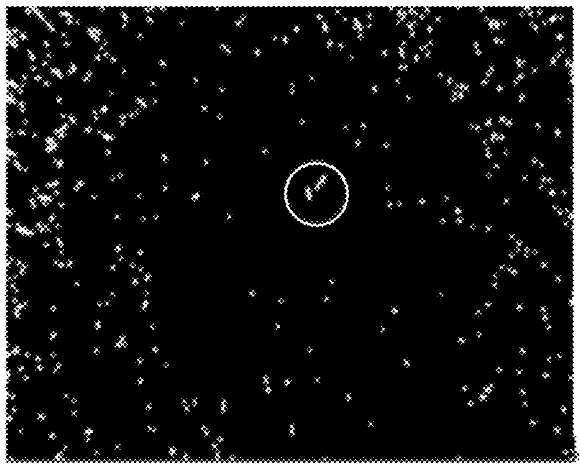
FIG. 3 shows a difference in a red component.

As a result, the images from which translation component has been removed shown in FIG. 2 were obtained, and the difference in the red component shown in FIG. 3 was detected. Then, through the steps (b) to (f), the blood flow rate was determined from the blood flow video of the gastric subepithelial microvessel obtained using the magnifying endoscope.

Table 2 shows measurement results of the segment size in each frame and the blood flow rate in the segment.

TABLE 2

| Processing results | | | | |
|---|---|---|---|---|
| No | X coordinate of segment center | Y coordinate of segment center | Major axis of segment (pixel) | Flow rate (mm/s) |
| 1 | 2 | 32 | 6.69 | 0.59 |
| 2 | 2 | 40 | 5.08 | 0.45 |
| | | (Omission) | | |
| 161 | 315 | 172 | 15.62 | 1.39 |
| 162 | 330 | 165 | 12.74 | 1.13 |
| | | (Omission) | | |

To measure the blood flow rate in real time, it is more preferable to use a personal computer with the blood flow measurement software described above installed and measure the blood flow by using an endoscopic video previously recorded.

The invention claimed is:

1. An endoscope system for measuring a blood flow rate of gastric subepithelial microvessel, the endoscope system comprising a magnifying endoscope and a blood flow video data processing unit for processing blood flow video data obtained using the magnifying endoscope, wherein the magnifying endoscope shoots a blood flow video of gastric subepithelial microvessel and transmits the blood flow video to the blood flow video data processing unit, and after receiving the blood flow video, the blood flow video data processing unit performs the following data processing:

decomposing the obtained blood flow video into frames;

removing a translation component by comparing an image of frame 1 and an image of a subsequent frame;

calculating a difference in a red component between the images from which the translation component has been removed, the calculating including setting a red component threshold, determining a difference between the red component of a pixel in frame 1 and a corresponding pixel in the subsequent frame, and calculating the difference in a red component between the images based only for pixels determined to have a difference greater than or equal to the red component threshold;

segmenting a part for which the difference in the red component has been calculated; and calculating a segment size of obtained segment data.

2. The endoscope system according to claim 1, wherein the blood flow video data is blood flow video data of a microvessel in a part of a gastric subepithelial suspected to have an abnormality obtained using the magnifying endoscope.

3. The endoscope system according to claim 2, wherein the endoscope system further performs processing of comparing an obtained blood flow rate of gastric subepithelial microvessel and a blood flow rate of normal gastric subepithelial microvessel.

4. The endoscope system according to claim 1, wherein the processing of removing a translation component is processing of detecting a difference between frames caused by a blood flow.

5. The endoscope system according to claim 1, wherein the processing of calculating the difference in the red component is to detect a movement of a red blood cell.

6. The endoscope system according to claim 1, wherein a segment generated by the segmentation is a segment through which a red blood cell passes between the frame 1 and the subsequent frame.

7. The endoscope system according to claim 1, wherein the calculation of the segment size is a calculation of a minor axis and a major axis of the segment.

8. The endoscope system according to claim 1, wherein a flow rate in each segment in the subsequent frame is calculated based on the segment size and a time between the frame 1 and the subsequent frame.

9. A method of measuring a blood flow rate in a gastric subepithelial microvessel, comprising:

obtaining a blood flow video of the gastric subepithelial microvessel taken using a magnifying endoscope;

decomposing the obtained blood flow video into frames;

removing a translation component by comparing an image of frame 1 and an image of a subsequent frame;

calculating a difference in a red component between the images from which the translation component has been removed, the calculating including setting a red component threshold, determining a difference between the red component of a pixel in frame 1 and a corresponding pixel in the subsequent frame, and calculating the difference in a red component between the images based only for pixels determined to have a difference greater than or equal to the red component threshold;

segmenting a part for which the difference in the red component has been calculated; and calculating a segment size of obtained segment data.

10. The measuring method according to claim 9, wherein the blood flow video is a blood flow video of a microvessel in a part of a gastric subepithelial suspected to have an abnormality obtained using the magnifying endoscope.

11. The measuring method according to claim 10, further comprising:

comparing an obtained blood flow rate of gastric subepithelial microvessel and a blood flow rate of normal gastric subepithelial microvessel.

12. The measuring method according to claim 9, wherein the removing the translation component is detecting a difference between frames caused by a blood flow.

13. The measuring method according to claim 9, wherein the calculating the difference in the red component is to detect a movement of a red blood cell.

14. The measuring method according to claim 9, wherein the segmentation generates a segment through which a red blood cell passes between the frame 1 and the subsequent frame.

15. The measuring method according to claim 9, wherein the calculation of the segment size is performed by calculating a minor axis and a major axis of the segment.

16. The measuring method according to claim 9, wherein a flow rate in each segment in the subsequent frame is calculated based on the segment size and a time between the frame 1 and the subsequent frame.

17. A system for measuring a blood flow rate, the system comprising a blood flow video data processing unit for processing blood flow video data, wherein the blood flow video data processing unit performs the following data processing:

decomposing a blood flow video into frames;

removing a translation component by comparing an image of frame 1 and an image of a subsequent frame;

calculating a difference in a red component between the images from which the translation component has been removed; the calculating including setting a red component threshold, determining a difference between the red component of a pixel in frame 1 and a corresponding pixel in the subsequent frame, and calculating the difference in a red component between the images based only for pixels determined to have a difference greater than or equal to the red component threshold segmenting a part for which the difference in the red component has been calculated; and calculating a segment size of obtained segment data.

* * * * *